(12) United States Patent
Johansen et al.

(10) Patent No.: US 7,957,004 B2
(45) Date of Patent: Jun. 7, 2011

(54) INTERFERENCE FILTER

(75) Inventors: Ib-Rune Johansen, Oslo (NO); Alain Ferber, Haslum (NO); Odd Løvhaugen, Oslo (NO); Håkon Sagberg, Oslo (NO)

(73) Assignee: Sinvent AS, Trondheim (NO)

( * ) Notice: Subject to any disclaimer, the term of this patent is extended or adjusted under 35 U.S.C. 154(b) by 105 days.

(21) Appl. No.: 11/911,627

(22) PCT Filed: Apr. 3, 2006

(86) PCT No.: PCT/NO2006/000123
§ 371 (c)(1),
(2), (4) Date: May 19, 2008

(87) PCT Pub. No.: WO2006/110041
PCT Pub. Date: Oct. 19, 2006

(65) Prior Publication Data
US 2008/0273208 A1    Nov. 6, 2008

(30) Foreign Application Priority Data
Apr. 15, 2005   (NO) .................................. 20051850

(51) Int. Cl.
*G01B 9/02*    (2006.01)
*G02F 1/03*    (2006.01)

(52) U.S. Cl. ........................................ 356/454; 359/260
(58) Field of Classification Search .................. 356/454, 356/480, 519; 359/260, 359, 585, 578, 579
See application file for complete search history.

(56) References Cited

U.S. PATENT DOCUMENTS

| | | | |
|---|---|---|---|
| 3,930,718 A | 1/1976 | Jensen | |
| 3,939,348 A | 2/1976 | Barrett | |
| 4,309,108 A * | 1/1982 | Siebert | 356/519 |
| 5,151,585 A * | 9/1992 | Siebert | 250/201.9 |
| 5,218,422 A | 6/1993 | Zoechbauer | |
| 5,289,314 A * | 2/1994 | Siebert | 359/586 |
| 5,550,373 A | 8/1996 | Cole et al. | |

(Continued)

FOREIGN PATENT DOCUMENTS

DE    4334578 A1    4/1995
(Continued)

OTHER PUBLICATIONS

Zochbauer et al., "Fabry-Perot-Korrelationsphotometer fur de Gasanalyse", Technisches Messen, 1994, pp. 195-203, XP9069567A.

(Continued)

*Primary Examiner* — Hwa S. A Lee
(74) *Attorney, Agent, or Firm* — Rothwell, Figg, Ernst & Manbeck, P.C.

(57) ABSTRACT

This invention relates to an interference filter, especially for use in gas detection with infrared light within a chosen range, comprising at least two essentially parallel and partially reflective surfaces with a chosen distance between them thus defining a cavity delimited by the reflecting surfaces between which the light may oscillate, and wherein at least one of said surfaces is partially transparent for transmission of light to or from said cavity. The filter comprises a first transparent material having a high refractive index, e.g. silicon, positioned in at least a part of said cavity, and at least one of said reflective surfaces being divided into a three dimensional pattern with varying shift relative to its plane, thus to provide a position dependent resonance condition between them for separation of different wavelengths in the light.

13 Claims, 13 Drawing Sheets

U.S. PATENT DOCUMENTS

| | | | |
|---|---|---|---|
| 5,646,729 A | 7/1997 | Koskinen et al. | |
| 5,886,247 A | 3/1999 | Rabbett | |
| 5,920,391 A | 7/1999 | Grasdepot et al. | |
| 6,016,199 A * | 1/2000 | Newton | 356/519 |
| 6,246,480 B1 * | 6/2001 | O'Brien | 356/454 |
| 6,500,521 B2 * | 12/2002 | O'Brien | 428/156 |
| 6,590,710 B2 | 7/2003 | Hara et al. | |
| 6,768,097 B1 | 7/2004 | Viktorovitch et al. | |
| 6,853,654 B2 | 2/2005 | McDonald et al. | |
| 7,142,573 B2 | 11/2006 | Lunt et al. | |
| 7,426,040 B2 * | 9/2008 | Kim et al. | 356/519 |
| 7,460,302 B2 | 12/2008 | Amitai | |
| 2003/0035121 A1 * | 2/2003 | Nebendahl et al. | 356/519 |
| 2003/0058520 A1 | 3/2003 | Yu et al. | |
| 2004/0080832 A1 | 4/2004 | Singh | |
| 2005/0094699 A1 | 5/2005 | Lunt et al. | |

FOREIGN PATENT DOCUMENTS

| | | |
|---|---|---|
| EP | 0069368 A2 | 1/1983 |
| EP | 0693683 A1 | 1/1996 |
| EP | 1126256 A2 | 8/2001 |
| GB | 2286041 A | 8/1995 |
| JP | 2001228022 A | 8/2001 |
| JP | 2005031326 A | 2/2005 |
| WO | 8702470 A1 | 4/1987 |
| WO | 9309422 A1 | 5/1993 |
| WO | 9621140 A1 | 7/1996 |
| WO | 9814804 A1 | 4/1998 |

OTHER PUBLICATIONS

Hohlfeld et al., "A Thermally Tunable, Silicon-Based Optical Filter," Sensors and Actuators, vol. A 103, pp. 93-99, 2003.

International Search Report, International Application No. PCT/NO2006/000124, dated Jul. 28, 2006, 3 pages.

Translation of Japanese Office Action, issued in JP 2008-506394 on Feb. 22, 2011, 4 pages.

* cited by examiner

INTERFERENCE FILTER

This invention relates to an interference filter, especially for use in gas detection with infrared light within a chosen range.

Most gases absorb infrared light with photon energies corresponding to the allowed vibrational transitions of the gas molecule. When measuring gas concentrations with infrared light it is usual to perform two measurements of the light transmitted through the gas: One measurement being influenced (reduced) by gas absorption and one reference measurement which is not affected by the gas. This measurement method is sometimes referred to as non-dispersive infrared (NDIR).

Figure 1:
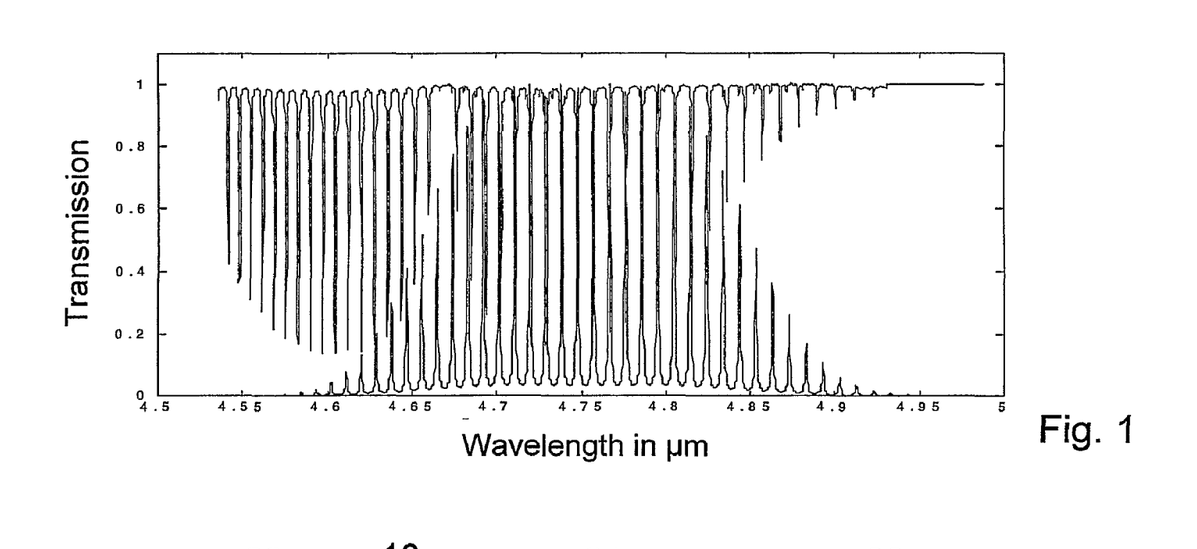
FIG. 1 illustrates as mentioned above the transmission spectrum for CO, and for a Fabry-Perot filter.
Figure 2:
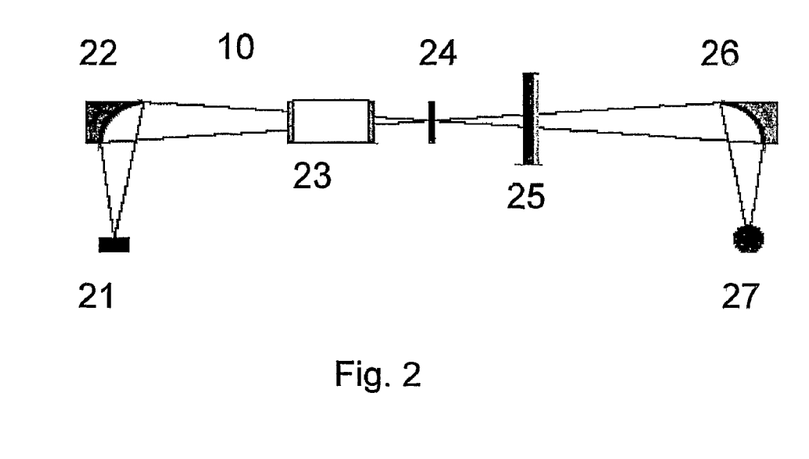
FIG. 2 illustrates as mentioned above a usual assembly for performing gas measurements according to the known art.

As illustrated in FIG. 1, which shows the transmission as a function of the wavelength in the range of 4.5-5.0 μm, the infrared spectrum of carbon monoxide (CO) has an almost periodic line pattern. Several gases, including methane ($CH_4$), have similar absorption lines. The distance between the CO lines increases with increasing wavelength, but is essentially constant within a small interval of wavelengths. In order to measure the concentration of CO one may use an assembly as illustrated in FIG. 2. Light from an infrared source 21 is sent via a collimating or focusing mirror 22 through a gas cell 23 and further through a modulated filter 24, e.g. a Fabry-Perot filter, and a fixed band pass filter 25, and further through a focusing mirror 26 to a detector 27. In this line up the function of the modulated filter is to shift between two configurations or settings. In one setting it transmits light in the spectral range where the CO transmits light (correlation setting) and in the other setting the it transmits light in the range where the CO absorbs light (anti-correlation setting). In this way it is possible to shift continuously between measurements using the different settings. The difference between the two settings will be zero when CO is not present in the gas cell, and will increase with increasing concentration of CO.

By using a filter being adapted to single lines in the gas spectrum several advantages may be obtained:
1) A given gas concentration gives a larger relative change in the measured signal, compared to when a band pass filter is used.
2) If other gases are present which absorbs within the same wavelength range, these will have minimal influence on the measurements, as one reduces the sensitivity for gases in the same range but with different lines.
3) Changes in the source temperature and other disturbances will also affect both measurements to the same degree.

For this to work everything except the position of the filter lines must be kept constant. This may be obtained by letting the light follow as similar paths as possible. Preferably everything affecting the measurements should have the same influence on them. In addition to other gases, influences may be temperature gradients, dirt deposited on optical surfaces, drift in amplifier circuits, mechanical stability etc.

It is difficult to make a filter which fits directly with the CO lines. A good approximation is an interference filter having two parallel optical surfaces with a distance d between the surfaces, and a refractive index n for the medium between the surfaces. The transmission through the filter is then a periodic function of the wave number $v=1/\lambda$, where $\lambda$ is the wavelength. The period is ½nd, where n is the refractive index. Now the distance d, may be chosen so that the period corresponds with the CO lines in one range in the spectrum. When the optical wavelength s=nd is changed with one fourth of the wavelength: $s\pm(\Delta s)=s\pm\lambda/4$, the required modulation of the filter is obtained. With a constant refractive index this will correspond to a change in thickness $d\pm(\Delta d)=d\pm\lambda/4n$. When the refractive index is 1, $\Delta d$ will be approximately 2.3 μm.

Transmission through an interference filter in anti-correlation mode, adapted to the CO spectrum, is described in FIG. 1 where the upper line shows the CO spectrum and the lower line shows the transmission spectrum of the filter, both as functions of the wavelength, which is in the range of 4.5 to 5.0 μm.

Out from the centre wavelength a gradually increasing deviation will occur between the filter lines and the gas lines, as shown in FIG. 1. By adding a band pass filter one can delimit the range which is used.

If the interference filter is to consist of two parallel mirrors with an adjustable distance, the choice in optical materials between the mirrors is very limited: Air, other gases or possibly an elastic, transparent material. The optical material in the interference filter dictates how large angular spread one may have in the incoming light. When the angle increases the effective optical wavelength will decrease for the interfering light, and a spread in the incident angles will result in a smearing of the transmission spectrum. A high refractive index will give a low maximum refracted angle inside the filter material. The maximum allowed angle will decide the etendue of the filter. Etendue is the product of area and solid angle of the light bundle, a measure of how much light it is possible to get through the system when the radiation source has unlimited extension. It can be shown that for a given spectral resolution the etendue is proportional to the square of the refractive index. Thus one may get 10 times more light if e.g. silicon is used (n=3.4) instead of air in the resonator.

The challenge is to make an interference filter with high refractive index, in which one also may change the optical wavelength enough to adjust the filter into both correlation and anti-correlation modes.

Previous Work.

The principle of measuring carbon monoxide with such an interference filter is described in U.S. Pat. No. 3,939,348 from 1974. It is also mentioned the possibility for making a thermally modulated filter in a transparent optical material, but silicon or similar is not mentioned.

It is expensive to make a mechanical interferometer, and therefore this measuring method has been unsuitable for cheap, mass produced CO sensors for use e.g. in fire alarms for the home market and process monitoring of incinerators.

Around 1990 Michael Zochbauer did some experiments with heating of a silicon disc for changing the optical wavelength, see Zochbauer M. 1994. *Technisches Messen* 61: 195-203. This way the interference filter becomes a cheap component. The heating and cooling cycle turned out to be slow and energy consuming. Also, it was difficult to achieve a uniform temperature over the disc.

Thus it is an object of this invention to provide an interference filter with maximum light throughput which also makes it possible to perform correlation and anti correlation measurements under as similar situations as possible, e.g. by fast switching between two interference conditions or possibly to make it possible to monitor them simultaneously.

These objects are obtained using an filter according to the accompanying claims.

The invention will be described in more detail below with reference to the accompanying drawings which illustrates the invention by way of examples.

FIGS. 5A,B illustrates the principle of the diffractive filter in FIG. 3.

DESCRIPTION OF THE INVENTION

Figure 3:
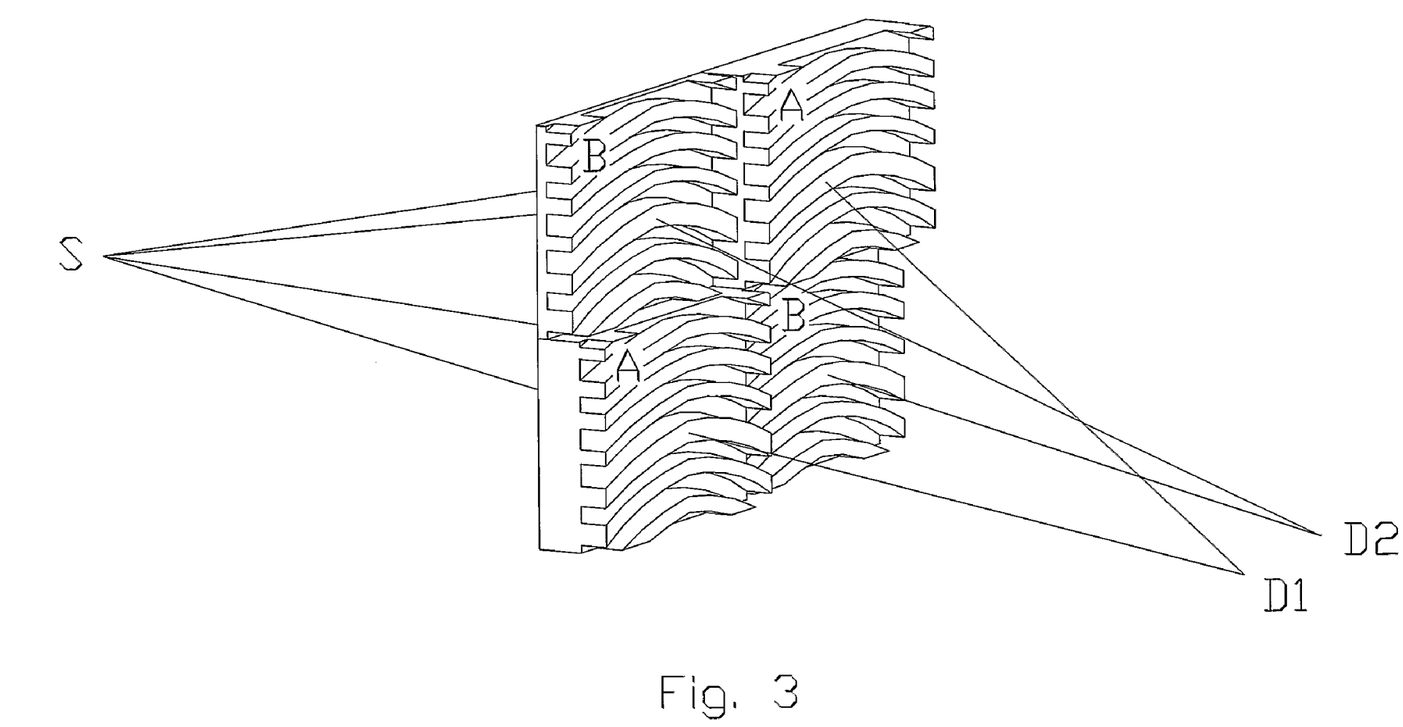
FIG. 3 illustrates a preferred embodiment of the invention provided with a diffractive filter.
Figure 4A:
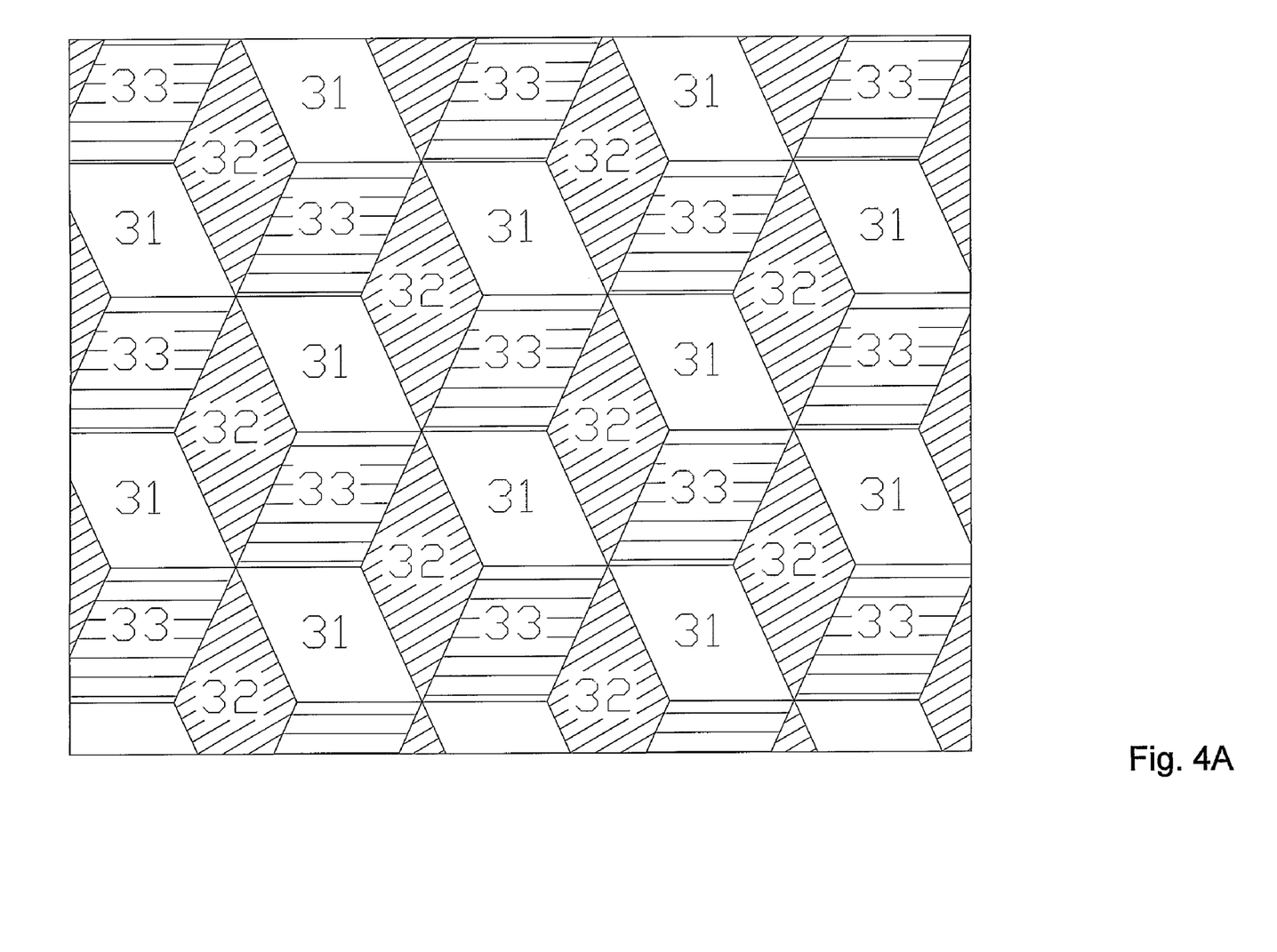
FIGS. 4A-C illustrates an embodiment of the invention comprising three different filters.
Figure 4B:
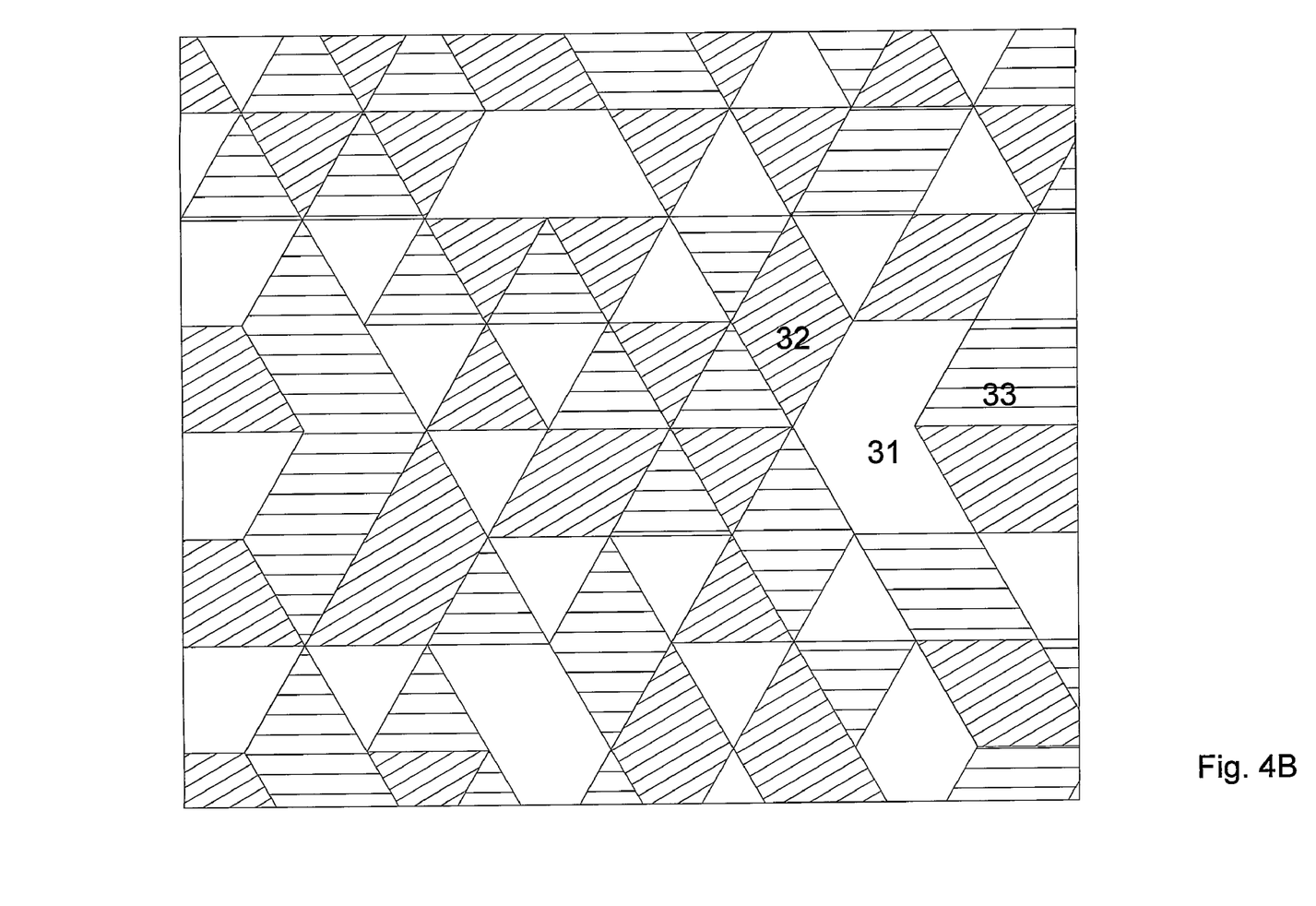
Figure 4C:
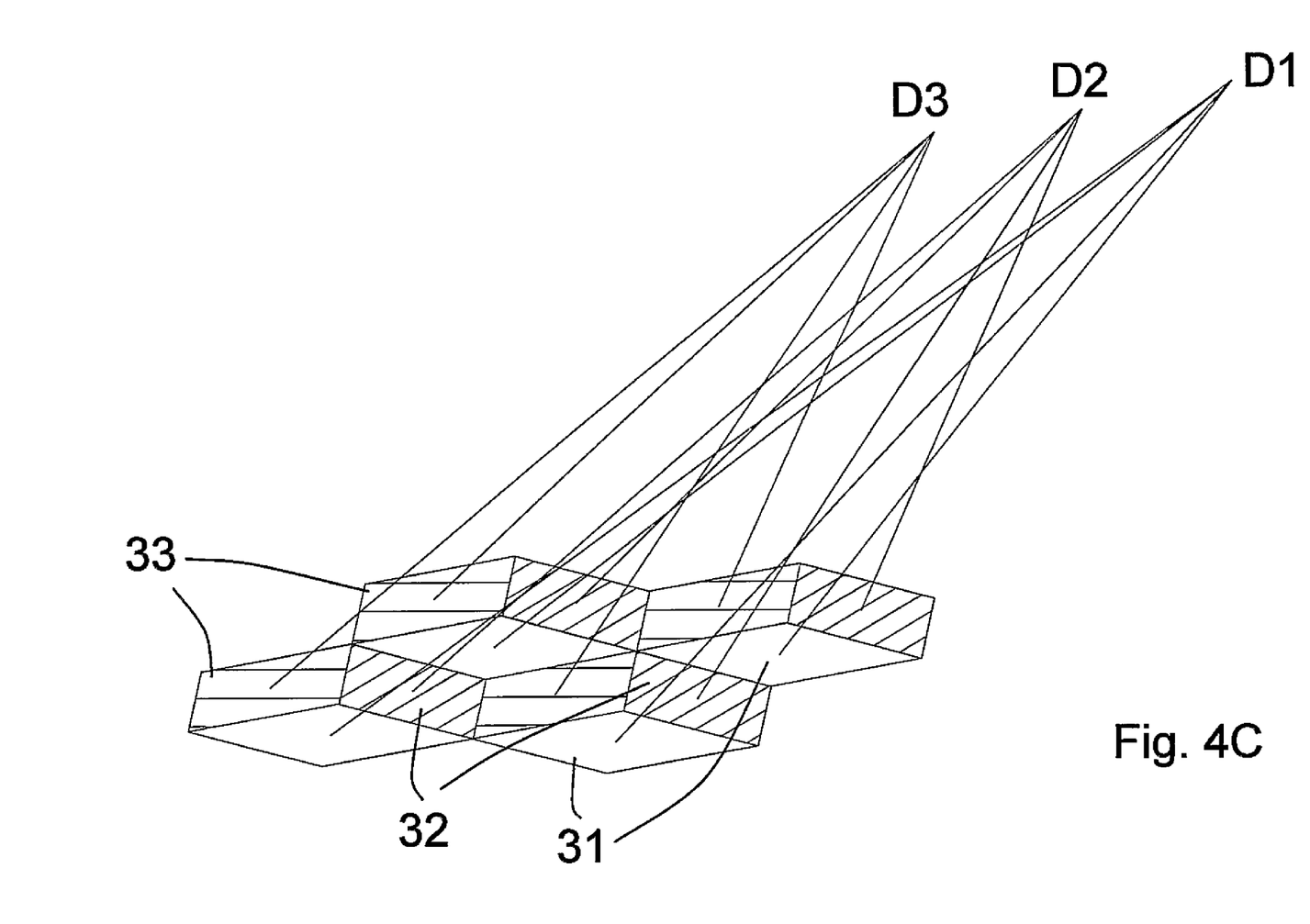

FIG. 3 shows the principle of the present invention. The silicon disc 1 is divided into a mosaic pattern (only shown with four squares) in which the difference in optical wavelength between the squares A is one quarter of a wavelength longer than through the squares B. Instead of modulating the filter, two different interference filters are now used, where the light is distributed depending on the filter it has passed through. The mosaic pattern of A and B filters is preferably distributed as evenly as possible over the filter with respect to the light beam, so as to avoid systematic errors following e.g. uneven gas distribution in the beam path. The figure shows thus four mosaic parts defining two different thicknesses of the Fabry-Perot filter. The proportions in the figure are exaggerated of illustration purposes. Using more than two different thicknesses has the advantage that a larger temperature drift (and thus changes in optical pathlength) can be tolerated while still being able to extract a usable signal difference. FIGS. 4A,4B,4C shows mosaics of three different interference filter segments, with different thicknesses 31,32,33, tiled in a regular and a random fashion. As illustrated in FIG. 4C the light that has passed through a single filter segments may be directed, e.g. by a diffractive lens relief, to one of three foci D1,D2,D3.

Referring again to FIG. 3 the light coming from the source S and is thus distributed between the parts of the substrate having different thickness, so that a parallel and simultaneous filtering of the light beam is provided on the light beam passing through the filter. One may filter out different wavelengths, or wavelength sets, in the same light beam in different positions of the interference filter. These different wavelengths may then be separated with other types of filtering, so that a simultaneous measurement on different sets of wavelengths may be provided, e.g. by providing lenses on the filter surfaces focusing in different directions as illustrated in FIG. 3.

The partially reflective and partially transmitting surfaces on the material may be produced in several ways, but according to a preferred embodiment of the invention they are simply constituted by plane and essentially parallel surfaces between air and silicon, which gives a reflectance of 0.3. If a better finesse is required, or there is a need for depositing other materials on the reflecting surfaces, other per se known methods may be used to make reflective surfaces. Also, other materials, such as Germanium, may be used as alternative to silicon. This has a higher refractive index than silicon and will require other adaptations being obvious for a person skilled in the art.

As mentioned above FIG. 3 also illustrates a preferred embodiment of the invention in which a diffractive pattern is provided which focus the light passing through the thin filters B to D2 and from the thick filters A to another point D1. To measure the filtered light one may either use one single detector or multiple detectors. When multiple detectors are used, each detector is placed at one of the focal points corresponding to a set of filter tiles or elements. When a single detector is used, a scanning device is necessary. Examples of scanning devices or methods are: Tiltable mirrors, translation of the detector, or rotation or translation of the filter assembly. Other solutions for separating the light with different wavelengths may also be contemplated, such as a mask for separating the light from one part of the mosaic pattern at the time.

The signal difference will depend on whether CO is present, thus resulting in a system corresponding to the thermally or micromechanically modulated filter.

A constructional challenge is that the filter has to act like an optical resonator on the inside. This means that even if a focusing diffractive pattern is deposited on the outside the phase shifts an internal reflection must be independent of position, i.e. as for a mirror.

If a diffractive lens or grating is used as illustrated in FIG. 3 to separate light from different positions on the interference filter there is also a possibility for adding an additional wavelength dependent filtering by using the dispersion in the filter. This is per se known art and will not be described in any detail here.

Figure 6A:
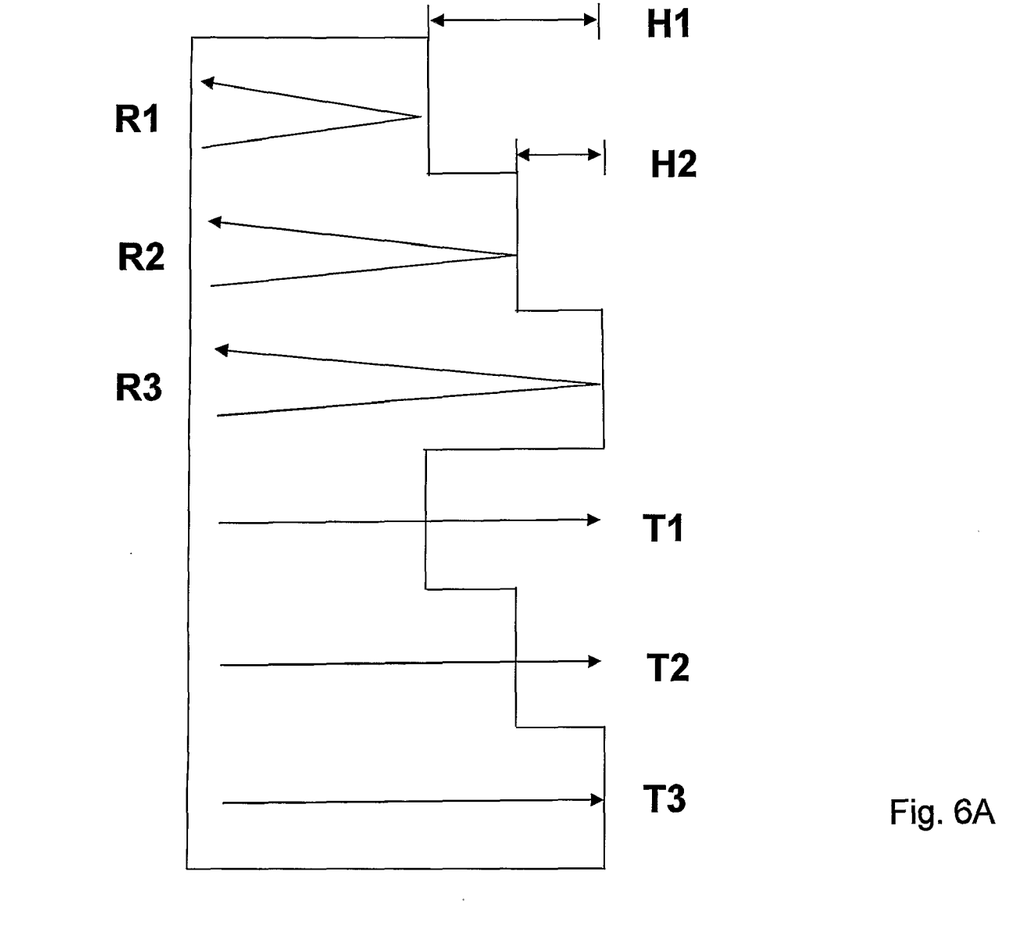
FIG. 6 illustrates an embodiment of the invention being usable as a band pass filter.

FIG. 6A shows a cross section of the diffractive pattern mentioned above in more detail, and shows a transmitting filter wherein the inner phase condition is fulfilled. At the same time a suitable set of three different phase delays are obtained being usuable as a diffractive lens. Thus there is a diffractive pattern with three different heights in two steps H1,H2, so that the light reflected from these three levels on the surface 11 has three different phase shifts R1,R2,R3 when it reaches the entrance surface 12. The height of each step is half the wavelength divided by the refractive index in silicon (n=3,427), i.e. about 670-690 nm depending on where in the CO spectrum one has chosen. Then the phase shift at internal reflections becomes zero, 1 or two wavelengths, depending on the local height in the pattern. The light propagating out of the silicon disc T1,T2,T3 get a phase shift of 0, 0.29 or 0.64 wavelengths for the corresponding heights. This makes it possible to make a diffractive lens with an efficiency of between 0.6 and 0.7.

Figure 5:
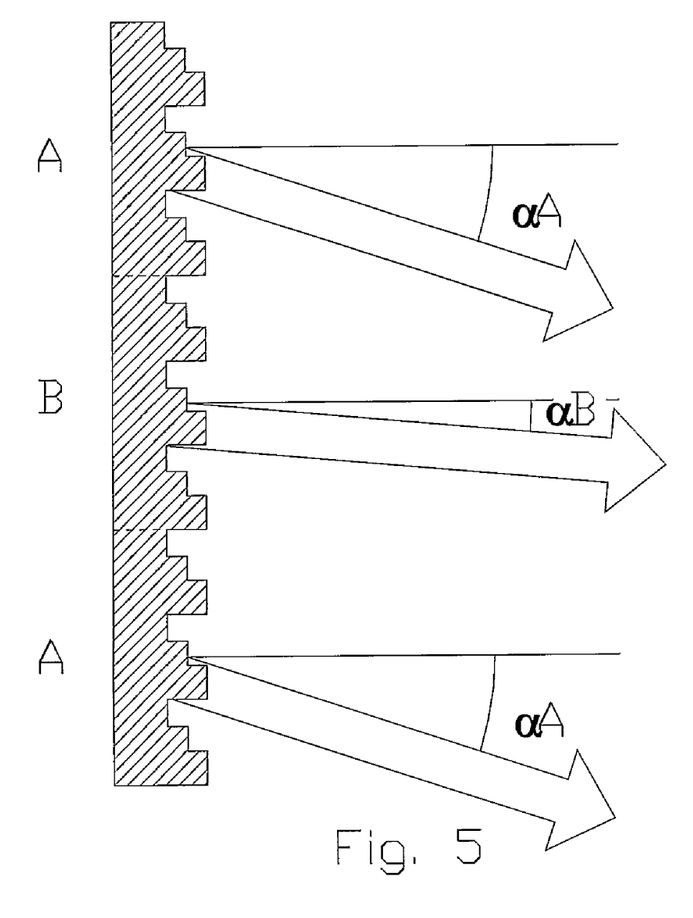

FIG. 5 illustrates the invention comprising both the diffractive pattern and the mosaic, where in addition to the height differences related to the diffractive pattern there is the height differences between the different parts of the mosaic. In FIG. 5 the shown case is halve the step height in the diffractive pattern, i.e. around 340 nm, resulting in a total of six levels. In FIG. 5 it is illustrated how each part of the mosaic is provided with a diffractive pattern for controlling the light beams. If the optical path length through the disc is increase with a quarter of a wavelength the line pattern is shifted with half a period. The difference in height between the parts of the mosaic may be etched on one or both sides of the disc. In the drawing the diffractive pattern is the diffractive pattern is shown as being repetitive, but this may be provided in a number of different ways as lenses or gratings.

Figure 6B:
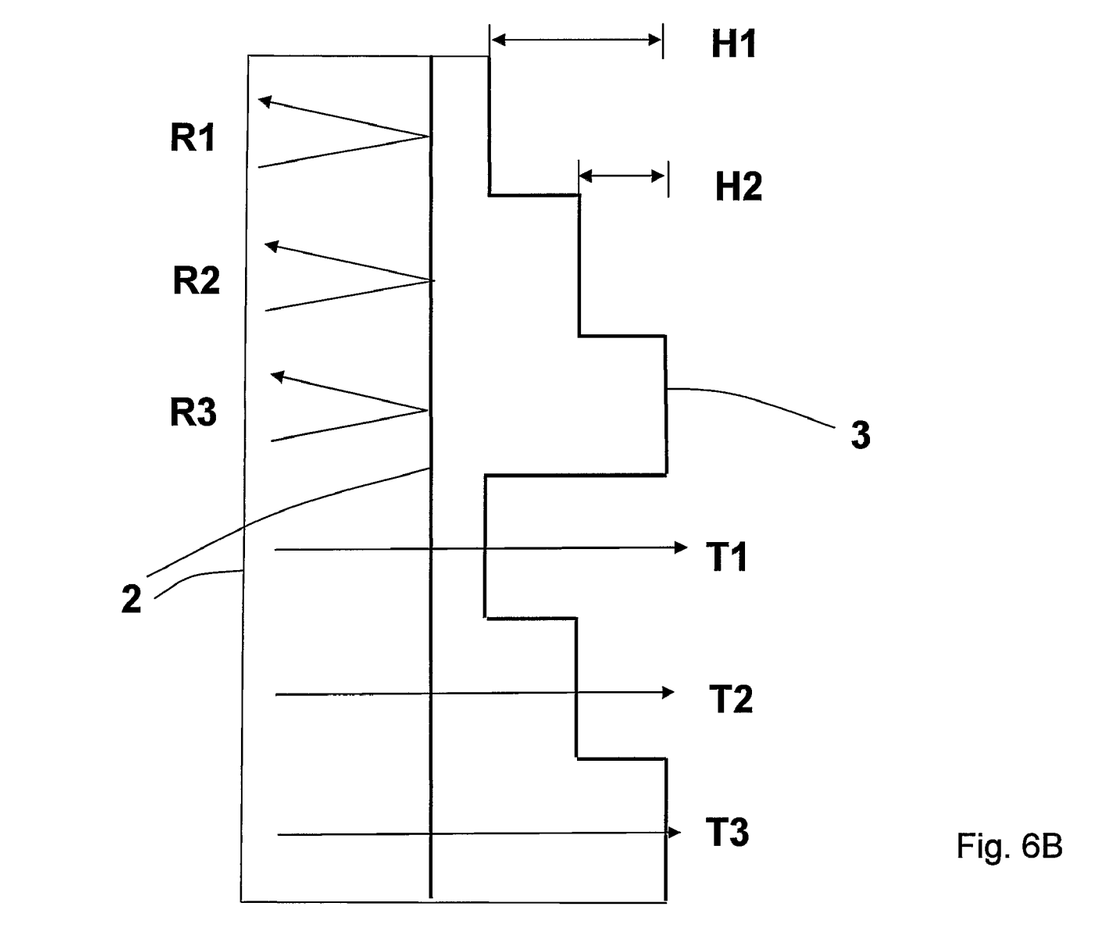

The one partially reflecting surface 2 may also be a buried layer with a diffractive pattern on the outside, as illustrated in FIG. 6B. Then the diffractive pattern should have an anti-reflective layer. In FIG. 6B the filter is a combination of a Fabry-Perot filter and a diffractive relief pattern which also may be used as a band pass filter.

The pattern may be produced using photolithography, resist masks and Deep Reactive Ion Etching (DRIE) or dry etching. The dry etching process consists essentially of two electrodes which together provide an electrical field. A gas is pumped into the field, and ions are accelerated toward the surface to be etched. The accelerated ions dominate over the radicals in the recombination, and an anisotropic etching profile is obtained.

Standard tolerances for disc thickness are usually not sufficient to let the filter lines meet the CO lines immediately. In addition the optical thickness varies with the temperature. Temperature control is beneficial, but proper choice of the number and thicknesses of interference filters may also ensure that a usable signal can always be found as a difference of intensities measured at the focal spots. If temperature control is to be used it may be advantageous if the temperature of the filter is higher than the maximum temperature of the environment, so that the required thickness may be obtained by heating. The disadvantage is that each sensor must be calibrated, and that the heating is power consuming.

Figure 7A:
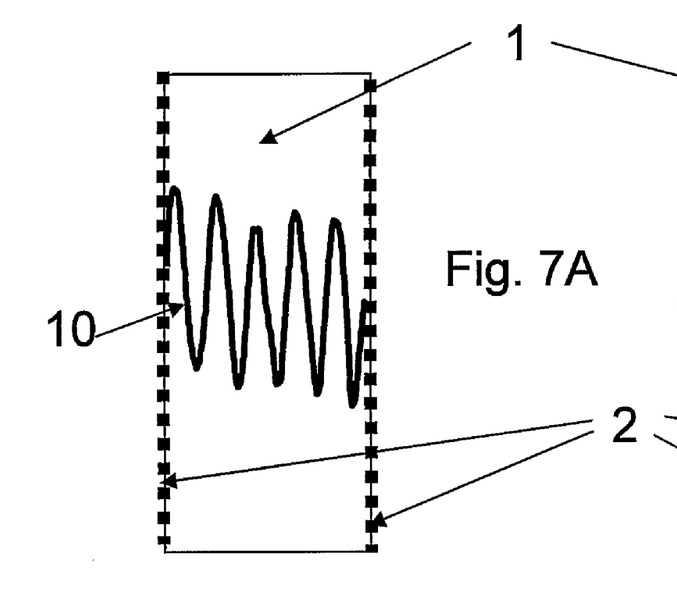
FIGS. 7A,7B illustrates a detail of an alternative embodiment of the present invention, as well as the optical equivalent of this embodiment.
Figure 7B:
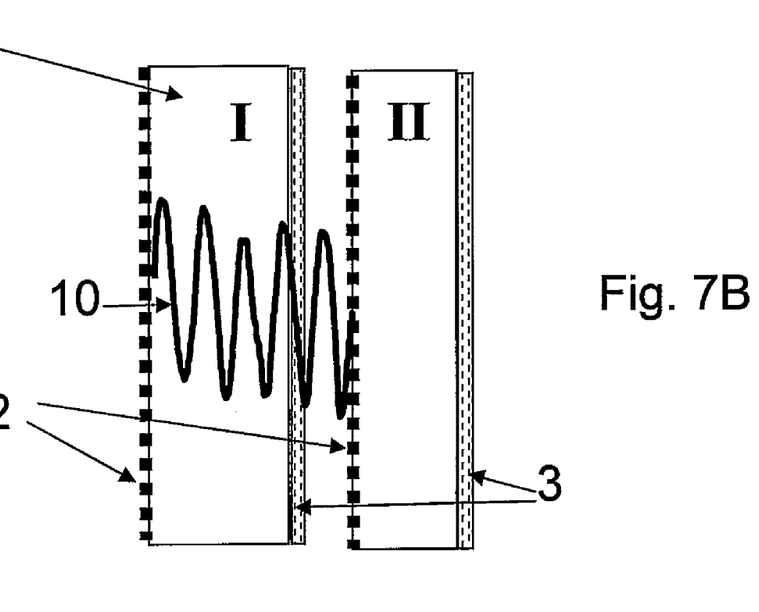

In FIG. 7B a cross section of an interference filter is illustrated consisting of two silicon discs which may provide and alternative or addition to the heat calibration. The dominating interference is between the two transitions 2 between silicon and air. On the other side of the discs an anti-reflection layer 3 is positioned. The result of this is that the interference filter will function/look like a single silicon disc 1, as illustrated in FIG. 7A, except for an "invisible" cavity. By changing the cavity, meaning the distance between the surfaces, the total optical path length between the surfaces 2 giving the interference changes. Then the filter may be set in both correlation and anti-correlation modes, so that one achieves the flexibility of an interferometer using cavity and mirrors, at the same time as the advantages of the silicon material are maintained, i.e. high angles of incident and reduced total thickness. The reduced thickness and short cavity distance makes it generally easy to make parallel surfaces.

The cavity only has to be large enough to enable practical adjustment in the range of $\lambda/4$ to $\lambda/2$, depending on the tolerance and stability of the actual embodiment, and will usually contain air, but may be filled with a flexible material, for example a gel with a chosen refractive index to increase the efficiency of the filter.

The anti-reflection layer may consist of one or more layers of different refractive indexes. This is per se known technology and will not be described in any detail here, but may be provided as a 0.65 µm layer of SiO with operation at wavelengths in the range of 4.75 µm. Other techniques such as porous silicon or gradual transitions in refractive index may also be used. The most important is that is has minimal reflection coefficient for the wavelength range of interest. The remaining reflection coefficient will affect the two measurements differently.

Figure 8:
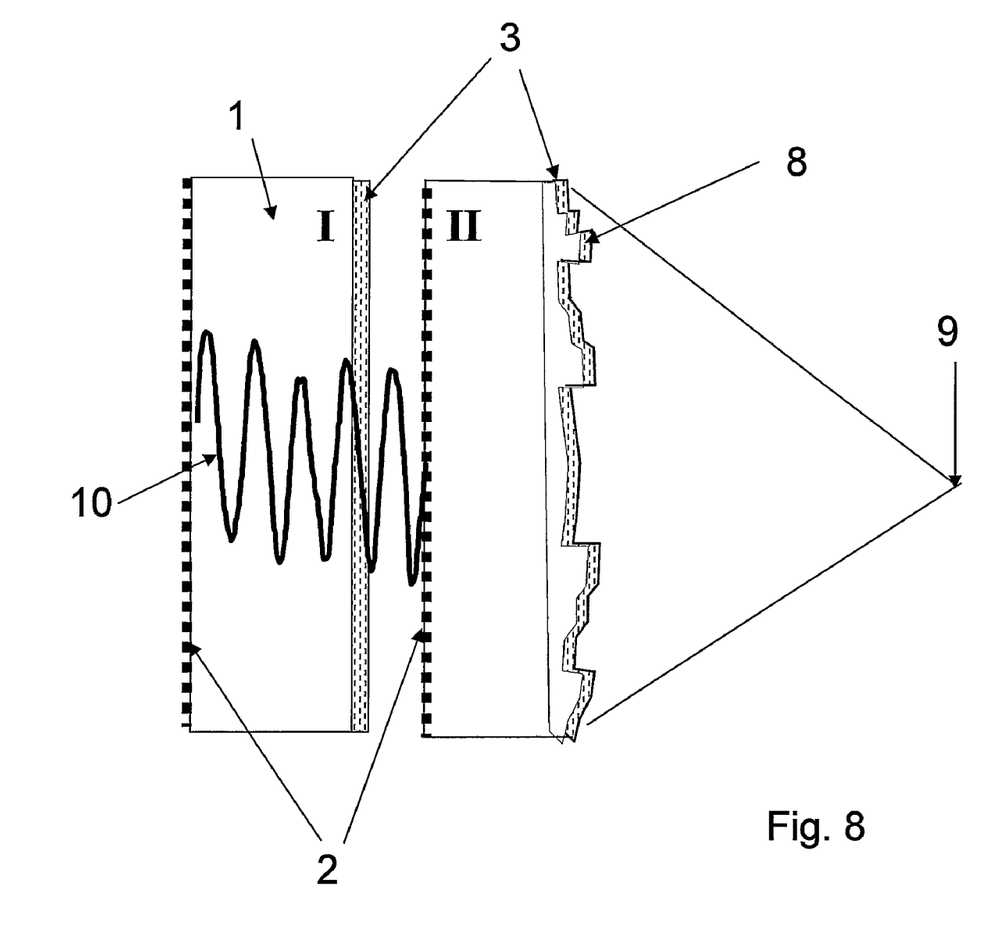
FIG. 8 illustrates the embodiment in FIG. 6 more in detail provided with a diffractive lens.

In FIG. 8 it is shown how the solution in FIG. 7 can be provided with a diffractive lens with the same design as the grating in FIG. 6, but with an air gap in front of the partially buried reflective layer. The lens, being adapted to focus the light toward a point 9, may be split in a mosaic pattern so that the parts having the corresponding levels constitutes parts of the same lens and focus toward the same point.

Figure 9:
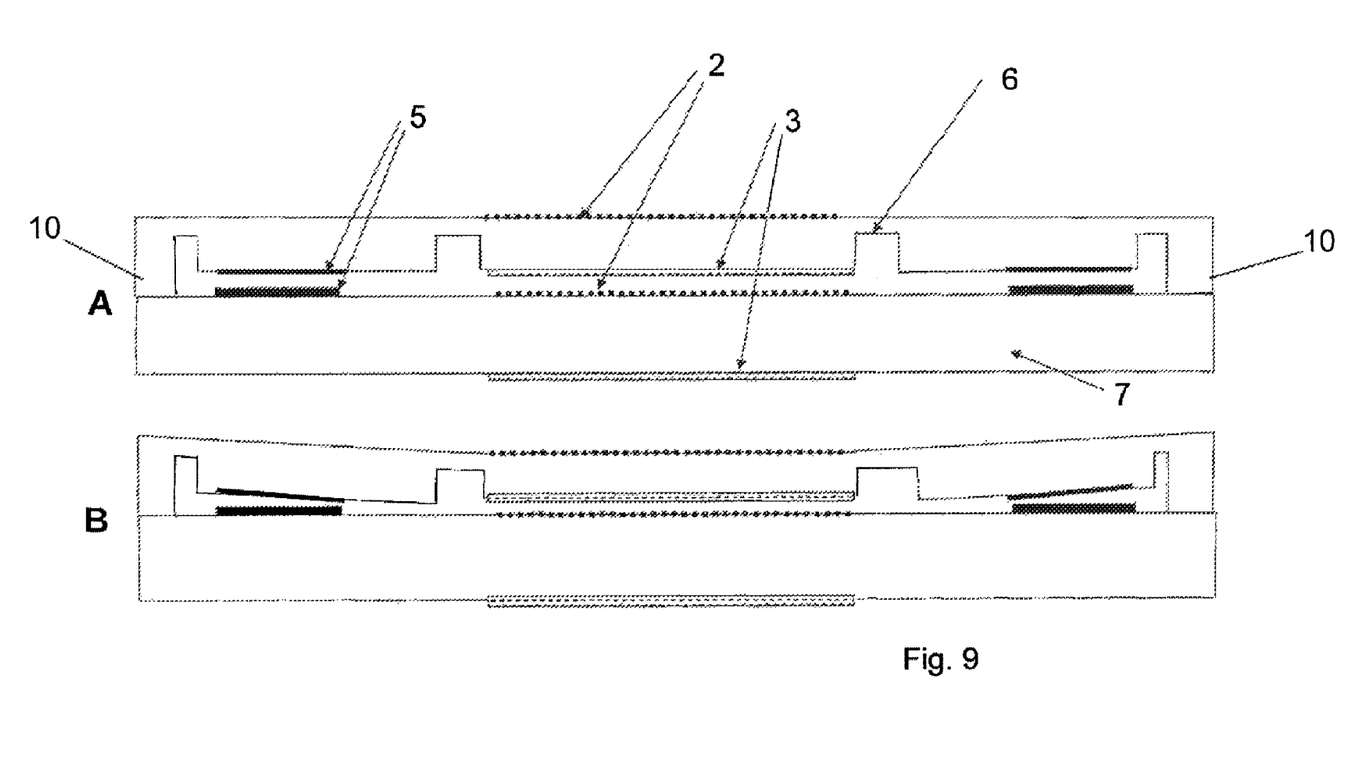
FIG. 9 illustrates a micro mechanical embodiment of the invention.

FIGS. 9A and B shows sketches of how the filter is thought to be implemented based on per se known solutions for wafer bonding and micromachining. As is evident the filter here is constituted by a substrate with a disc 6 being held at a chosen distance over the substrate 7 by perimeter portions 10 of the disc 6 to form a cavity between one of the reflective surfaces 2 and the transparent material covered by anti-reflection layer 3. By applying an electrical voltage between the silicon disc 6, which constitutes one of the reflectors 2 and the transparent material in the filter, and the underlying substrate 7 with the second reflector, one may adjust the distance between them with electrostatic attraction, as is seen from the difference between figure A and B. Thus the thickness of the cavity is changed in a simple way. In FIG. 9 electrodes 5 are included for applying a potential between the parts. As the filter is preferably transmitting it is also provided with an anti-reflection layer on the lower side of the substrate, which is also in a transmitting material, preferably silicon. In FIG. 9 the dimensions in the different directions are out of proportion compared to a practical realizable embodiment, this being for illustration purposes. This solution is described more in detail in simultaneously filed Norwegian patent application No. 2005.1851, as well as the international application filed with priority from said application, which is included here by way of reference.

Figure 10A:
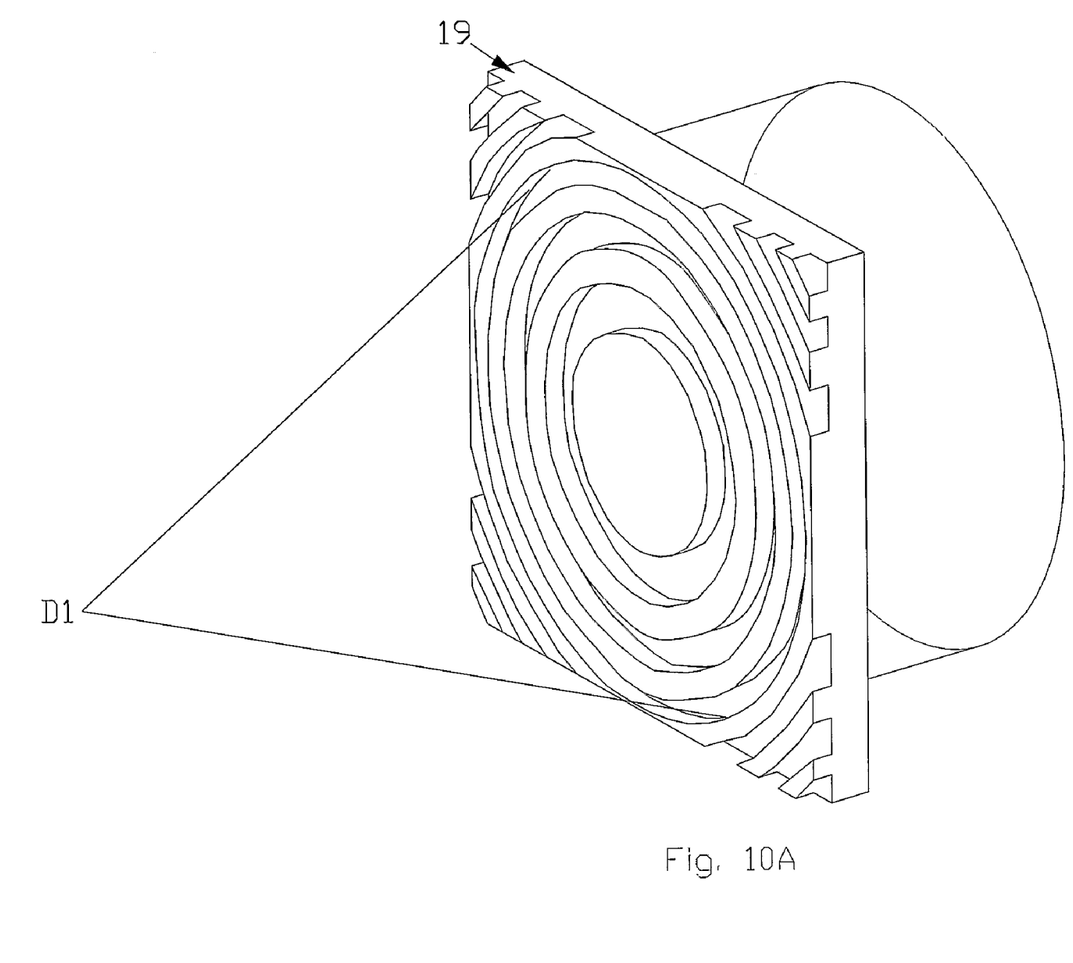
FIGS. 10A,B illustrates use of the solution in FIG. 6.
Figure 10B:
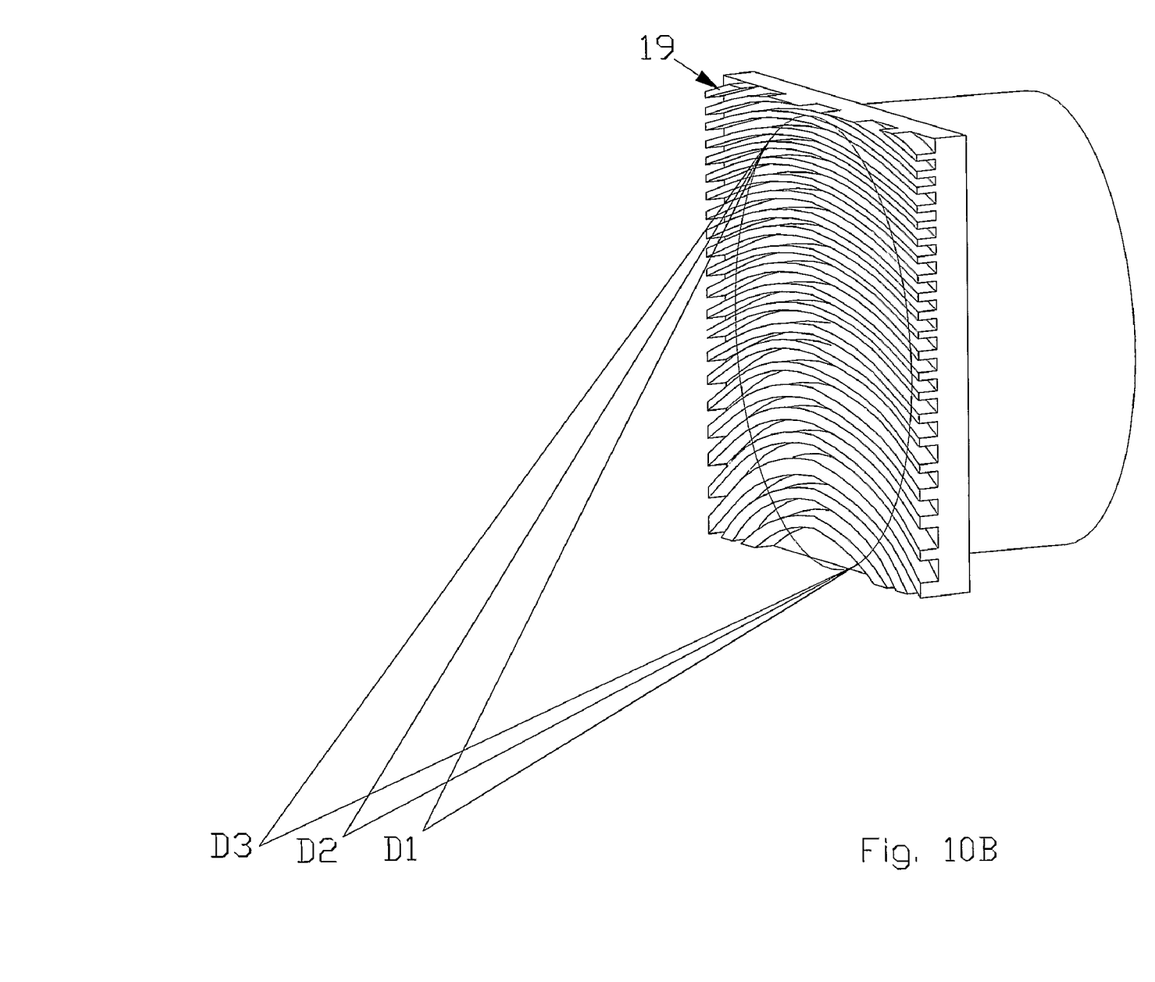

FIGS. 10A and 10B illustrates how the diffractive pattern 19 may provide focusing toward a point where the focus D1,D2,D3 depends on the wavelength of the light. In FIG. 10A a diffractive lens with one focal point D1 is illustrated, and in FIG. 10B it is illustrated how the diffractive lens is asymmetric, only defining the outer regions of a lens, and provides three focal points D1,D2,D3 for different wavelengths. The asymmetric solution in FIG. 10B makes it possible to detect the intensity at the different focal points by positioning a sensor array in the optical axis of the diffractive lens. In that way one may separate the different wavelengths in the spectrum so that the band pass filter shown in FIG. 2 becomes unnecessary. In practice the different parts may therefore have different diffractive patterns, preferably so that the parts having the same cavity length in the Fabry-Perot filter has the same type of diffractive filter, so as to distinguish its wavelength range. The details of how the diffractive lenses are constructed is part of the known art and is e.g. discussed in international patent application No WO 02/44673.

The invention claimed is:

1. Interference filter, especially for use in gas detection, using infrared light within a chosen range of wavelengths, comprising at least two essentially parallel reflective surfaces with a chosen distance between them thus defining a resonator delimited by the reflective surfaces between which the light may oscillate, and wherein at least one of said reflective surfaces is partially transparent for transmission of light to or from said resonator, wherein the filter comprises:

a first transparent material having a refractive index comparable to the refractive index of silicon or higher, positioned in at least a part of said resonator and the first transparent material being provided with at least one of said reflective surfaces, wherein one of said reflective surfaces includes a pattern being divided into at least two surface parts disposed in different planes at different distances from another reflective surface, thus providing at least two different optical path lengths between the reflective surfaces giving resonance at different wavelengths, and wherein said filter comprises an additional pattern on at least one of said reflective surfaces, the additional pattern comprising a diffracting relief pattern adapted to provide a diffractive grating for diffraction of at least two wavelengths in at least two directions.

2. Filter according to claim 1, wherein a first reflective surface is constituted by a mosaic pattern of essentially plane surface parts wherein each surface part defines one reflector in a Fabry-Perot interferometer with a chosen resonance wavelength, in which a second reflective surface constitutes a second reflector in the Fabry-Perot interferometer.

3. Filter according to claim 1, wherein said diffracting relief pattern constitutes a diffractive lens for focusing light with different wavelengths toward different points.

4. Filter according to claim 1, wherein said pattern is divided into at least two surface parts is provided on one side of a silicon disc.

5. Interference filter, especially for use in gas detection, using infrared light within a chosen range of wavelengths, comprising at least two essentially parallel reflective surfaces with a chosen distance between them thus defining a resonator delimited by the reflective surfaces between which the light may oscillate, and wherein at least one of said reflective surfaces is partially transparent for transmission of light to or from said resonator, wherein the filter comprises:
- a first transparent material having a refractive index comparable to the refractive index of silicon or higher, positioned in at least a part of said resonator and the first transparent material being provided with at least one of said reflective surfaces,
- wherein one of said reflective surfaces includes a pattern being divided into at least two surfaces, thus providing at least two different optical path lengths between the reflective surfaces giving resonance at different wavelengths,
- means for defining a distance between the first transparent material and at least one of said reflective surfaces to form a cavity between the first transparent material and at least one of said reflective surfaces,
- an adjustment device for adjusting said distance and thus provide a cavity having at least one dimension that may be chosen, and
- a reflection reducing layer in a border surface between the first transparent material and the cavity.

6. Filter according to claim 5, wherein a first reflective surface is constituted by one side of said first transparent material, the reflection reducing layer being positioned on an opposite side relative to the first reflective layer and wherein a second reflective surface is positioned on a carrier material on an opposite side of said cavity.

7. Filter according to claim 6, wherein the first transparent material is positioned at a distance over the second reflective surface, so that the first reflective surface is on an upper side of the first transparent material and at least one reflection reducing layer is in position on a lower side of the first transparent material.

8. Filter according to claim 7, comprising means for coupling a voltage source with electrical conductors to each of the reflective surfaces, thereby being able to change the distance between them electrostatically.

9. Filter according to claim 5, wherein said reflection reducing layer comprises at least one layer of material with a refractive index differing from the cavity and the first transparent material refractive indexes, and with a thickness chosen to reduce reflections at said border surface within said chosen range of wavelengths.

10. Filter according to claim 5, wherein a first reflective surface is constituted by a mosaic pattern of essentially plane surface parts wherein each surface part defines one reflector in a Fabry-Perot interferometer with a chosen resonance wavelength, in which a second reflective surface constitutes a second reflector in the Fabry-Perot interferometer.

11. Filter according to claim 5, wherein said pattern divided into at least two surface parts is provided on one side of a silicon disc.

12. Interference filter for use in gas detection with light within a chosen range of wavelengths, comprising at least two essentially parallel reflective surfaces with a chosen distance between them thus defining a resonator delimited by the reflective surfaces between which the light may oscillate, and wherein at least one of said reflective surfaces is partially transparent for transmission of light to or from said resonator, wherein the filter comprises:
- a first transparent material having a chosen refractive index and a minimal reflection coefficient within the chosen wavelength range, positioned in at least a part of said resonator and the first transparent material being provided with at least one of said reflective surfaces,
- wherein one of said reflective surfaces includes a pattern being divided into at least two surfaces, thus providing at least two different optical path lengths between the reflective surfaces giving resonance at different wavelengths;
- means for defining a distance between the first transparent material and at least one of said reflective surfaces and thus form a cavity between the first transparent material and at least one of said reflective surfaces,
- an adjustment device for adjusting said distance and thus provide a cavity having at least one dimension that may be chosen; and
- a reflection reducing layer in a border surface between the first transparent material and the cavity.

13. Interference filter for use in gas detection with light within a chosen range of wavelengths, comprising at least two essentially parallel reflective surfaces with a chosen distance between them thus defining a resonator delimited by the reflective surfaces between which the light may oscillate, and wherein at least one of said reflective surfaces is partially transparent for transmission of light to or from said resonator, wherein the filter comprises:
- a first transparent material having a chosen refractive index and a minimal reflection coefficient within the chosen wavelength range, positioned in at least a part of said resonator and the first transparent material being provided with at least one of said reflective surfaces,
- wherein one of said reflective surfaces is constituted by a pattern formed in the first transparent material, said pattern being divided into at least two surface parts disposed in different planes at different distances from another reflective surface, thus providing at least two different optical path lengths between the reflective surfaces giving resonance at different wavelengths,
- wherein said filter comprises an additional pattern on at least one of said reflective surfaces, the additional pattern comprising a diffracting relief pattern adapted to provide a diffractive grating for diffraction of at least two wavelengths in at least two directions.

* * * * *